US012589029B2

(12) United States Patent
Jee

(10) Patent No.: US 12,589,029 B2
(45) Date of Patent: Mar. 31, 2026

(54) SAFETY VITREOUS BODY CUTTING DEVICE

(71) Applicant: THE CATHOLIC UNIVERSITY OF KOREA INDUSTRY-ACADEMIC COOPERATION FOUNDATION, Seoul (KR)

(72) Inventor: Dong Hyun Jee, Suwon-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 61 days.

(21) Appl. No.: 18/927,099

(22) Filed: Oct. 25, 2024

(65) Prior Publication Data

US 2025/0134711 A1     May 1, 2025

(30) Foreign Application Priority Data

Nov. 1, 2023     (KR) ........................ 10-2023-0149303

(51) Int. Cl.
*A61F 9/007*          (2006.01)
(52) U.S. Cl.
CPC .... *A61F 9/00763* (2013.01); *A61B 2217/005* (2013.01)
(58) Field of Classification Search
CPC .. A61F 9/00763; A61F 9/007; A61F 9/00736; A61B 2217/005; A61B 17/32002; A61B 2017/320028; A61B 2017/320032
See application file for complete search history.

(56) References Cited

U.S. PATENT DOCUMENTS

| | | | | | |
|---|---|---|---|---|---|
| 5,403,323 | A | * | 4/1995 | Smith ................. | A61F 9/00736 606/107 |
| 5,843,111 | A | * | 12/1998 | Vijfvinkel ........... | A61F 9/00754 606/171 |
| 7,316,676 | B2 | * | 1/2008 | Peyman .............. | A61F 9/00727 604/521 |
| 8,398,578 | B1 | * | 3/2013 | Zolli ........................ | A61M 1/85 606/107 |
| 10,391,206 | B2 | * | 8/2019 | Singh .................... | A61M 25/01 |

(Continued)

FOREIGN PATENT DOCUMENTS

| | | |
|---|---|---|
| CN | 113143582 A | 7/2021 |
| KR | 10-2022-0147852 A | 11/2022 |
| KR | 10-2023-0051640 A | 4/2023 |

*Primary Examiner* — Sarah A Long
(74) *Attorney, Agent, or Firm* — Bridgeway IP Law Group, PLLC; Jihun Kim

(57)          ABSTRACT

An embodiment relates to a safety vitreous body cutting device capable of safely removing only a vitreous body attached to a retina without damaging the retina. Here, the safety vitreous body cutting device includes a tubular body part, a cutter part, and a safety net part. The tubular body part is formed in a cylindrical shape, negative pressure is provided at the inside, and an open hole is formed on the outer circumferential surface of a distal end. The cutter part reciprocates along the axial direction of the tubular body part at the inside of the tubular body part to cut the vitreous body introduced into the open hole. The safety net part is provided at the distal end of the tubular body part, and allows the vitreous body to pass through, but prevents the retina tissue from passing through.

9 Claims, 9 Drawing Sheets

(56)             References Cited

U.S. PATENT DOCUMENTS

| 11,752,101 | B2 * | 9/2023 | Yamamoto | ............ | A61M 5/486 |
| | | | | | 604/27 |
| 11,896,523 | B2 * | 2/2024 | Pollack | ............ | A61B 17/00491 |
| 2020/0306082 | A1 * | 10/2020 | Jimenez Onofre | ..... | A61F 9/007 |
| 2024/0023986 | A1 * | 1/2024 | Cote | ....................... | A61F 9/007 |

* cited by examiner

SAFETY VITREOUS BODY CUTTING DEVICE

CROSS-REFERENCE TO RELATED APPLICATION

The present application claims priority to Korean Patent Application No. 10-2023-0149303, filed Nov. 1, 2023, the entire contents of which are incorporated herein for all purposes by this reference.

BACKGROUND

This research was supported by a grant of Patient-Centered Clinical Research Coordinating Center (PACEN) funded by the Ministry of Health & Welfare, Republic of Korea (grant number: RS-2025-02218330).

The disclosure relates to a safety vitreous body cutting device, and more specifically, to a safety vitreous body cutting device capable of safely removing only a vitreous body attached to a retina without damaging the retina.

The retina, which is a transparent, thin membrane located at the innermost part of the eyeball wall and in contact with a vitreous body inside the eyeball, acts as a primary visual information organ that converts optical information of objects into electrical signals and transmits images to the central visual area of the brain through the optic nerve.

Vitreous body resection is a representative retina surgery of resecting the vitreous body inside the eyeball. If bleeding occurs inside the vitreous body or retina detachment occurs, vitreous body resection is performed to eliminate the bleeding and reattach the detached retina.

When performing vitreous body resection, a vitreous body cutter (vitrector, cutter) is used to remove bleeding in the vitreous body and remove the vitreous body attached to the retina. In addition, when diabetic complications are severe in the eyes, it is called proliferative diabetic retinopathy, and the proliferative membrane that occurs in this case is removed with a vitreous body cutter. Likewise, the vitreous body cutter plays the most important role in the retina surgery.

The shape of the conventional vitreous body cutter is a cylindrical straw with a hole at the end and a blade attached to the hole. The blade cuts the vitreous body while making a linear reciprocating motion, and it is possible to suck up the cut vitreous body due to the negative pressure applied to the straw.

FIG. 1 is an exemplary view showing the removal of a vitreous body attached to a retina using a conventional vitreous body cutting device.

As shown in FIG. 1, there is a problem that, in order to remove a vitreous body 10 attached to a retina 20, the retina tissue may be detached from an eyeball 40 and may be sucked into a vitreous body cutter 30 and cut (A) when the conventional vitreous body cutter 30 approaches very close to the retina 20. The moment the retina tissue is cut, retina bleeding occurs, damaging the photoreceptor cells, etc., and may progress to retina detachment, and complications may occur, so the retina tissue should not be touched.

In particular, when performing a retina detachment surgery, the retina floats in the vitreous body cavity while detached from the eyeball wall, so the risk of the retina 20 getting caught in the vitreous body cutter 30 may increase. However, if the vitreous body cutter is not brought close to the retina, the vitreous body attached to the retina cannot be removed. If the vitreous body attached to the retina is left, retina detachment may recur and a second surgery may be required.

Likewise, removing only the vitreous body attached to the retina without damaging the retina is one of the main processes of learning and training retina surgery. However, even for experts, there is always a risk of causing complications by cutting the retina together while removing the vitreous body attached to the retina, so a safety vitreous body cutting technique that safely removes only the vitreous body attached to the retina without damaging the retina is required.

RELATED ART DOCUMENT

Patent Document

Republic of Korea Patent Publication No. 2022-0147852 (Published on Nov. 4, 2022)

SUMMARY

An aspect of the disclosure is to provide a safety vitreous body cutting device capable of safely removing only a vitreous body attached to a retina without damaging the retina.

The aspect of the disclosure is not limited to that mentioned above, and other aspects not mentioned will be clearly understood by those skilled in the art from the description below.

An embodiment of the disclosure provides a safety vitreous body cutting device, including: a tubular body part having a cylindrical shape, in which a negative pressure is provided at the inside and an open hole is formed on the circumferential surface of a distal end; a cutter part that reciprocates along the axial direction of the tubular body part at the inside of the tubular body part and cuts a vitreous body introduced into the open hole; and a safety net part that is provided at the distal end of the tubular body part and allows the vitreous body to pass through but prevents the retina tissue from passing through.

In an embodiment of the disclosure, the safety net part may have a disc-shaped sheet of which the central part is connected to the distal end of the tubular body part, and a plurality of through-holes formed through the sheet.

In an embodiment of the disclosure, the through-hole may be formed in a square shape with vertical and horizontal lengths of 0.09 to 0.11 mm each.

In an embodiment of the disclosure, the safety net part may be formed of silicone material and is formed to fold or unfold around the distal end of the tubular body part.

In an embodiment of the disclosure, the safety net part may have a first frame radially provided at the distal end of the tubular body part, and a second frame circumferentially provided to the first frame with different diameters to form a mesh together with the first frame.

In an embodiment of the disclosure, the safety net part may further have a third frame having one end connected to the first frame and the other end provided to slide along the axial direction of the tubular body part on the circumferential surface of the tubular body part, thereby allowing the first frame to fold or unfold around the distal end of the tubular body part.

In an embodiment of the disclosure, a sliding groove may be formed on the circumferential surface of the tubular body part to guide the other end of the third frame to be inserted and slide.

In an embodiment of the disclosure, the safety net part may be formed of silicone material and is formed to fold or unfold around the distal end of the tubular body part.

In an embodiment of the disclosure, the safety net part is formed of a shape memory polymer, and the safety net part, which is in a state of being folded around the distal end of the tubular body part, may deform in shape to unfold when inserted into the eye.

In an embodiment of the disclosure, the safety net part may be formed into a circle with a diameter of 6 to 7 mm.

According to an embodiment of the disclosure, only a vitreous body may pass through the through-hole or mesh of a safety net part, and retina tissue may not pass through. Accordingly, during a vitreous body cutting surgery, the retina tissue can be prevented from being introduced into an open hole of a tubular body part, and thus, only the vitreous body can be effectively removed without damaging the retina tissue.

The effects of the disclosure are not limited to the effects described above, and should be understood to include all effects that are inferable from the configuration of the disclosure described in the detailed description or claims of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
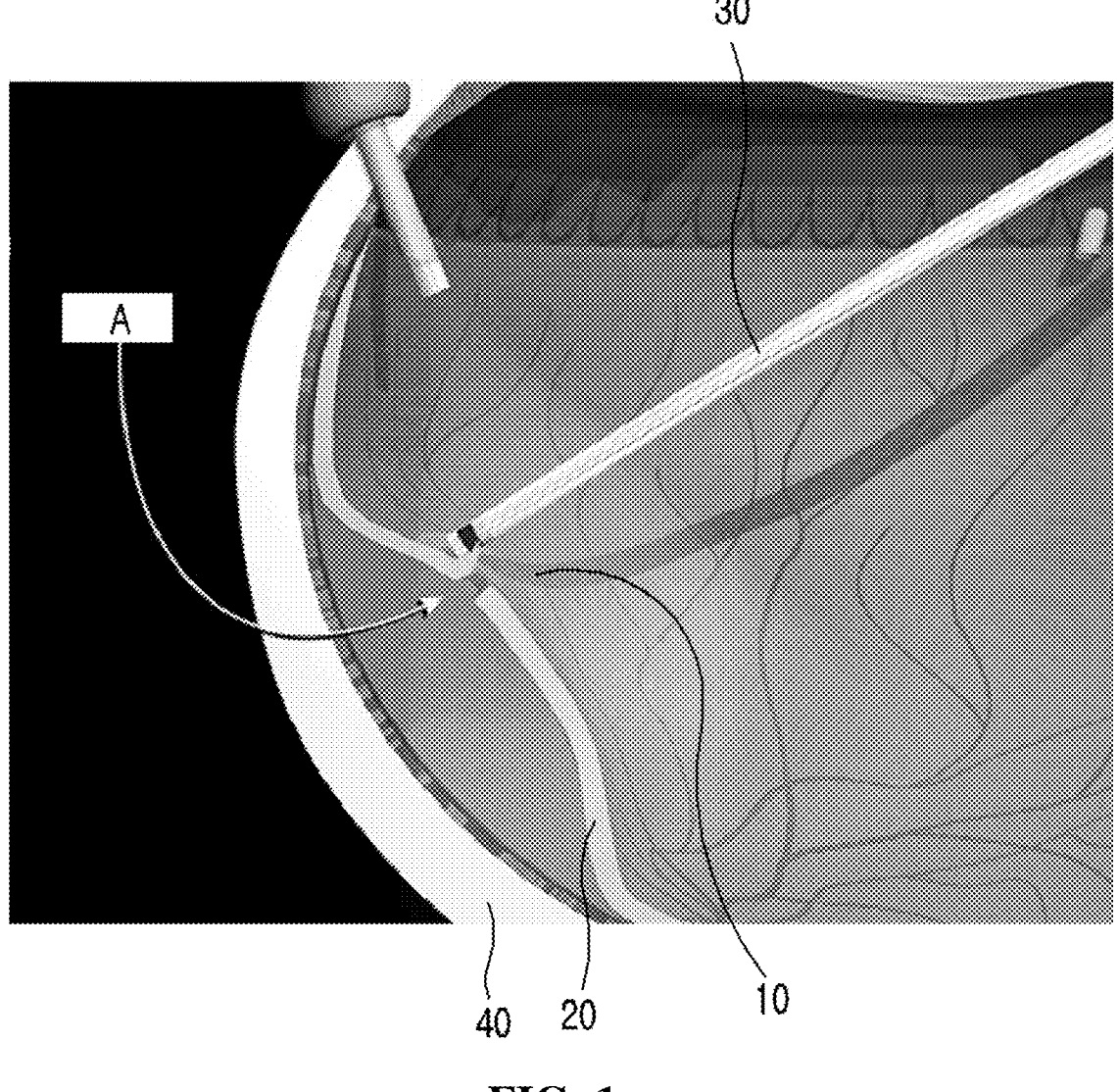
FIG. 1 is an exemplary view showing the removal of a vitreous body attached to a retina using a conventional vitreous body cutting device.

Hereinafter, the disclosure will be described with reference to the accompanying drawings. However, the disclosure may be implemented in various different forms, and therefore is not limited to the embodiments described herein. In addition, in order to clearly describe the disclosure in the drawings, parts that are not related to the description are omitted, and similar parts are given similar drawing reference numerals throughout the specification.

In the entire specification, when a part is said to be "connected (linked, contacted, coupled)" to another part, this includes not only the case where it is "directly connected" but also the case where it is "indirectly connected" with another member in between. In addition, when a part is said to "include" a certain component, this does not mean that other components are excluded unless otherwise specifically stated, but that other components may be additionally provided.

The terms used in this specification are used only to describe specific embodiments and are not intended to limit the disclosure. The singular expression includes the plural expression unless the context clearly indicates otherwise. In this specification, the terms "include" or "have" are intended to specify the presence of a feature, number, step, operation, component, part, or combination thereof described in the specification, but should be understood as not excluding in advance the possibility of the presence or addition of one or more other features, numbers, steps, operations, components, parts, or combinations thereof.

Hereinafter, embodiments of the disclosure will be described in detail with reference to the accompanying drawings.

Hereinafter, the disclosure will be described with reference to the accompanying drawings. However, the disclosure may be implemented in various different forms, and therefore is not limited to the embodiments described herein. In addition, in order to clearly describe the disclosure in the drawings, parts that are not related to the description are omitted, and similar parts are given similar drawing reference numerals throughout the specification.

In the entire specification, when a part is said to be "connected (linked, contacted, coupled)" to another part, this includes not only the case where it is "directly connected" but also the case where it is "indirectly connected" with another member in between. In addition, when a part is said to "include" a certain component, this does not mean that other components are excluded unless otherwise specifically stated, but that other components may be additionally provided.

The terms used in this specification are used only to describe specific embodiments and are not intended to limit the disclosure. The singular expression includes the plural expression unless the context clearly indicates otherwise. In this specification, the terms "include" or "have" are intended to specify the presence of a feature, number, step, operation, component, part, or combination thereof described in the specification, but should be understood as not excluding in advance the possibility of the presence or addition of one or more other features, numbers, steps, operations, components, parts, or combinations thereof.

Hereinafter, embodiments of the disclosure will be described in detail with reference to the accompanying drawings.

Figure 2:
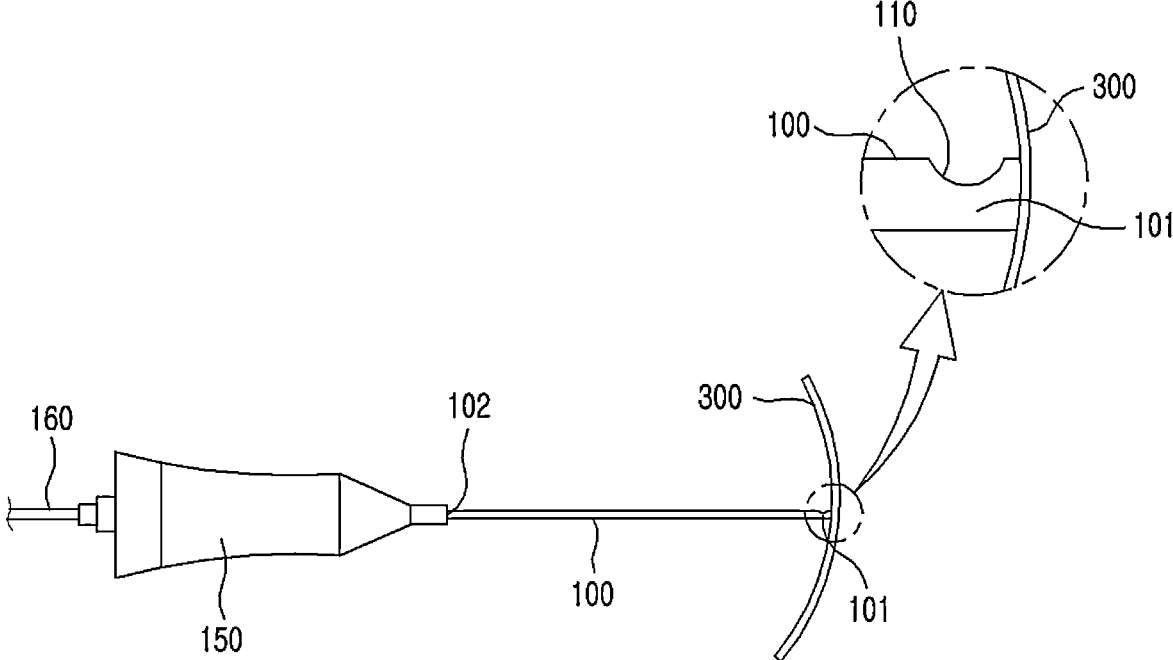
FIG. 2 is an exemplary view showing a safety vitreous body cutting device according to an embodiment of the disclosure.
Figure 3A:
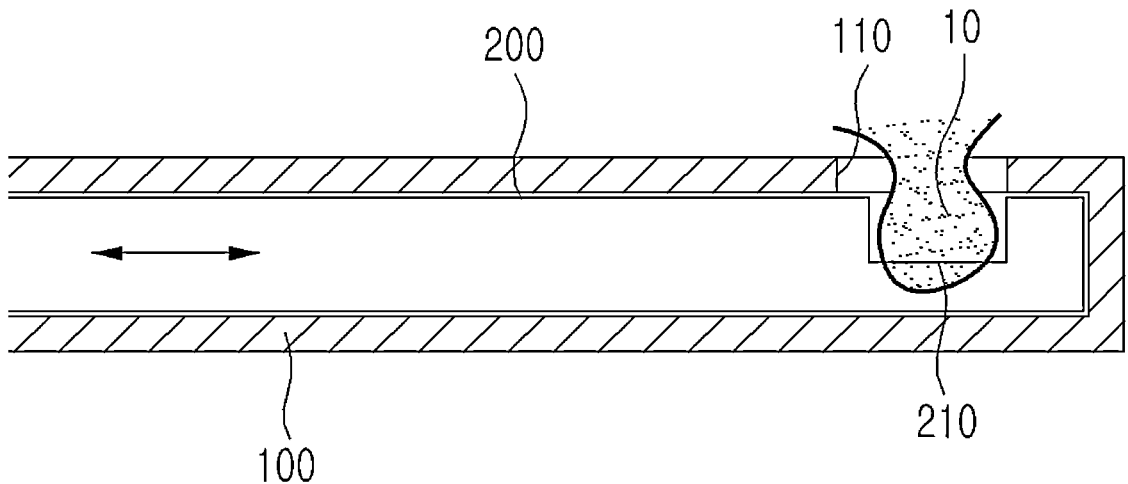
FIGS. 3A, 3B, and 3C are each an exemplary view for explaining an example of cutting a vitreous body using a safety vitreous body cutting device according to an embodiment of the disclosure.
Figure 3B:
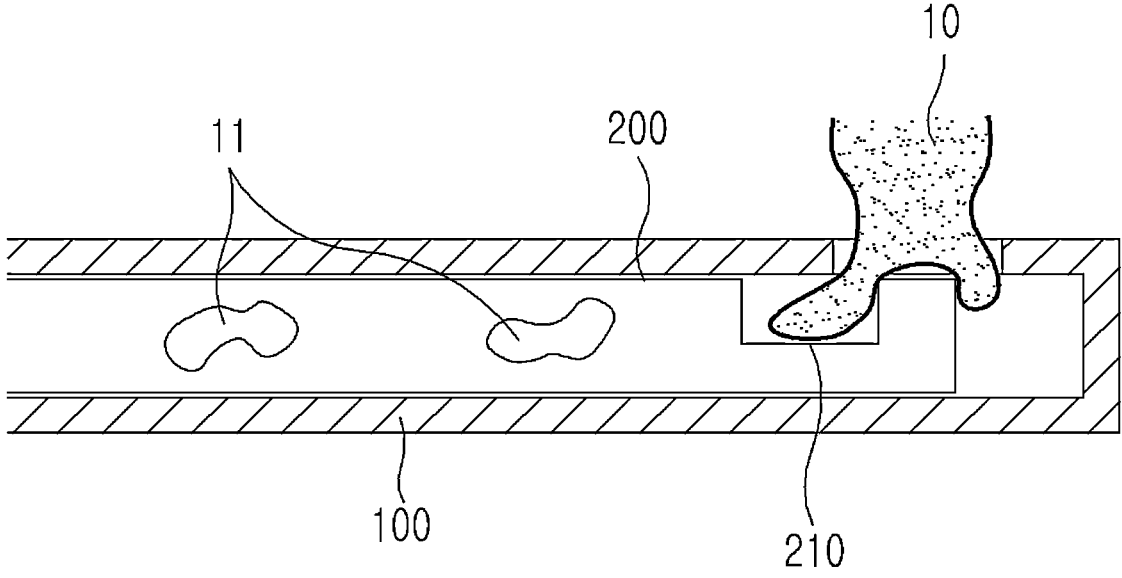
Figure 3C:
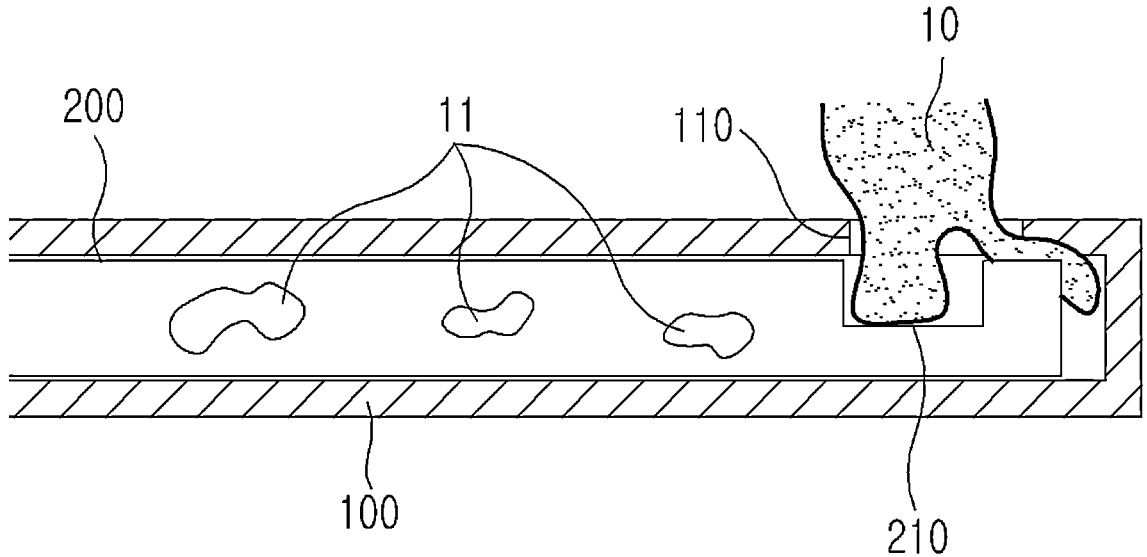

FIG. 2 is an exemplary view showing a safety vitreous body cutting device according to an embodiment of the disclosure, and FIGS. 3A, 3B, and 3C are each an exemplary view for explaining an example of cutting a vitreous body using a safety vitreous body cutting device according to an embodiment of the disclosure.

As shown in FIGS. 2, FIGS. 3A, 3B, and 3C, the safety vitreous body cutting device may include a tubular body part 100, a cutter part 200, and a safety net part 300.

The tubular body part 100 may be a cylindrical tube.

A handle 150 that a user may hold by hand may be coupled to a proximal end 102 of the tubular body part 100.

A suction tube 160 may be connected to the handle 150, and the suction tube 160 may be connected to the tubular body part 100. The suction tube 160 may be connected to an external suction pump (not shown), and negative pressure provided by the suction pump may be provided to the tubular body part 100.

In addition, an open hole 110 may be formed on the circumferential surface of the distal end of the tubular body part 100. The inside of the tubular body part 100 may be connected to the outside by the open hole 110.

The cutter part 200 may be provided at the inside of the tubular body part 100 and may be reciprocally moved along the axial direction of the tubular body part 100. In addition, the cutter part 200 may have a knife 210.

When the knife 210 is positioned to correspond to the open hole 110, a vitreous body 10 enters the open hole 110, and the cutter part 200 moves toward the proximal end 102 of the tubular body part 100, the knife 210 may cut the vitreous body 10. Then, the vitreous body may be sucked and moved to the inside of the tubular body part 100 by the negative pressure inside the tubular body part 100 (see FIGS. 3A and 3B).

Afterwards, the cutter part 200 may be moved again toward a distal end 101 of the tubular body part 100, so that the knife 210 may be positioned again in the open hole 110. In addition, when the vitreous body 10 enters the open hole 110 and the cutter part 200 moves toward the proximal end 102 of the tubular body part 100, the knife 210 may cut the vitreous body 10, and the vitreous body may be sucked and moved toward the inside of the tubular body part 100 (see FIG. 3C).

The safety net part 300 may be provided at the distal end 101 of the tubular body part 100.

In addition, the safety net part 300 may be formed to allow the vitreous body 10 to pass through, but prevent the retina tissue from passing through.

Figure 4:
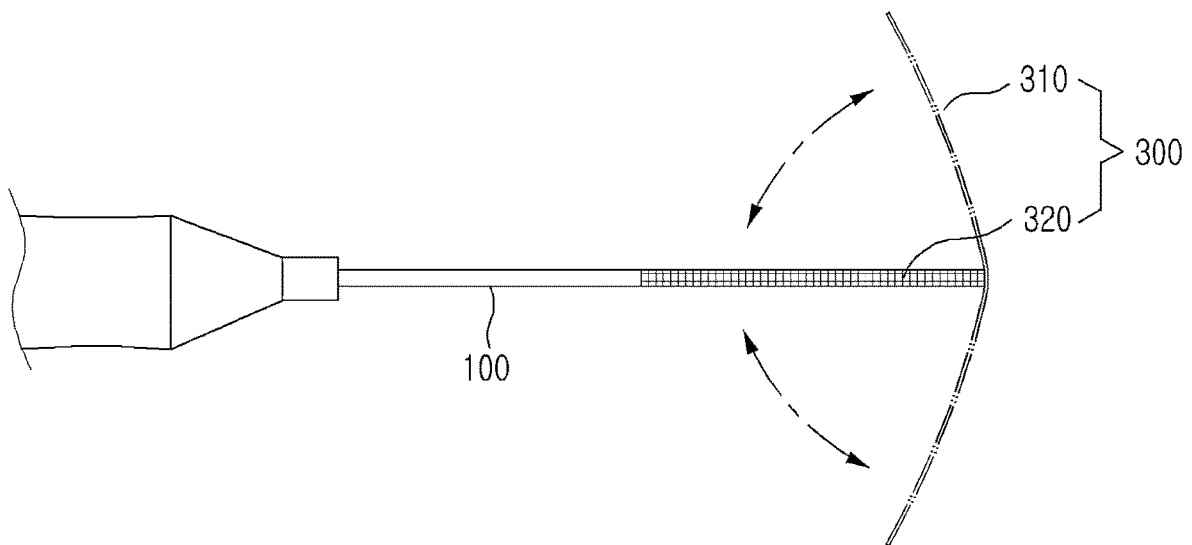
FIG. 4 is an exemplary view showing a folded state of a safety net part of a safety vitreous body cutting device according to an embodiment of the disclosure.
Figure 5:
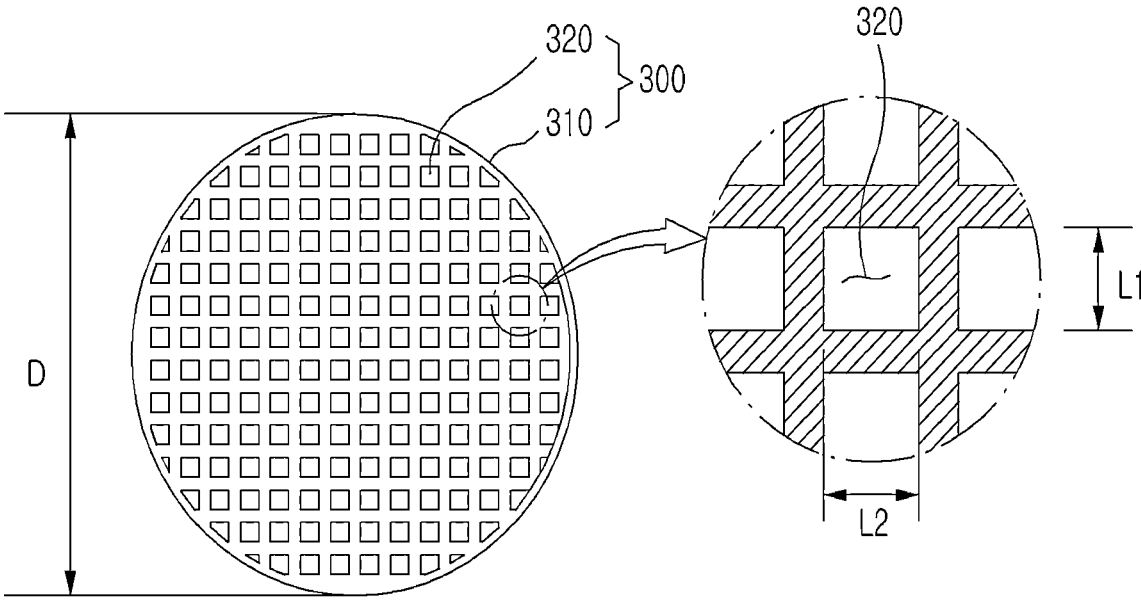
FIG. 5 is a frontal view showing a safety net part of a safety vitreous body cutting device according to an embodiment of the disclosure.

FIG. 4 is an exemplary view showing a folded state of a safety net part of a safety vitreous body cutting device according to an embodiment of the disclosure, and FIG. 5 is a frontal view showing a safety net part of a safety vitreous body cutting device according to an embodiment of the disclosure.

As shown in FIGS. 4 and 5, the safety net part 300 may have a sheet 310 and a through-hole 320.

The sheet 310 may be formed in a disk shape, and the central portion of the sheet 310 may be connected to the distal end 101 of the tubular body part 100.

In addition, a plurality of through-holes 320 may be formed through the sheet 310.

Since the safety net part 300 may come into contact with the retina, and thus may be formed of a biocompatible silicone material rather than a metal. In addition, the safety net part 300 formed of the silicone material may be folded or unfolded around the distal end 101 of the tubular body part 100.

Normally, when performing a vitreous body excision surgery, a corneal perforation (surgical wound) is made with a thickness of 25 to 27 G (gauge), and the safety net part 300, which is folded and attached to the tubular body part 100, may be unfolded after being inserted into the eye through the corneal perforation.

That is, in the basic state, the safety net part 300 is unfolded, and when the user folds the safety net part 300 by hand and inserts the folded safety net part 300 and tubular body part 100 into the corneal perforation, the safety net part 300 that has passed through the corneal perforation may be unfolded.

It is desirable that the silicone material forming the safety net part 300 have a certain level of strength. Preferably, the safety net part 300 may be formed of a silicone material having a Shore A hardness of about 25. Around the Shore A hardness of 25, ensured is soft yet firm enough strength, so the retina may be supported not to be sucked out, while maintaining softness and not damaging the retina.

The safety net part 300 may be formed into a circle with a diameter D of 6 to 7 mm.

That is, the diameter of the optic nerve is 1.5 mm, and by forming the diameter of the safety net part 300 to a size that is the radius of two optic nerves, it is possible to prevent a dangerous situation from occurring where the retina is attached to the outside of the safety net part 300.

In addition, by forming the diameter of the safety net part 300 to a size that is the radius of two optic nerves, it is possible to stably cut only the vitreous body while effectively supporting the retina. If the diameter of the safety net part 300 exceeds 7 mm, the control becomes dull, and there is a risk that the safety net part 300 may damage the retina. In summary, it is preferable that the safety net part 300 be formed in a circular shape with a diameter D of 6 to 7 mm.

In addition, if the size of the through-hole 320 is small, it is difficult for the vitreous body to pass through the through-hole 320 and be removed. On the other hand, if the size of the through-hole 320 is large, the retina tissue may be sucked out together and damaged. Therefore, it is preferable that the through-hole 320 be formed in a square shape with a vertical L1 and horizontal L2 length of 0.09 to 0.11 mm.

Only the vitreous body may pass through the through-hole 320 of the safety net part 300, and the retina tissue may not pass through. During vitreous body cutting surgery, the safety net part 300 may prevent retina tissue from being introduced into the open hole 110 of the tubular body part 100, and thus, only the vitreous body may be effectively removed without damaging the retina tissue.

In addition, the safety net part 300 may be formed to have a certain curvature in the unfolded state.

Meanwhile, the safety net part 300 may be in a folded state as a basic state, and may also be maintained in a folded state even after being inserted into the eyeball. The safety net part 300 that is maintained in a folded state even after being inserted into the eyeball may be usefully used in cases where a vitreous body in a narrow and deep area of the surgical field must be resected. That is, in cases of proliferative diabetic retinopathy or when removing the retina fibrous membrane, there are cases where vitreous body resection surgery must be performed in a narrow and deep groove. A safety net part 300 that remains folded even after being inserted into the eye may be effectively used in such cases.

Figure 6:
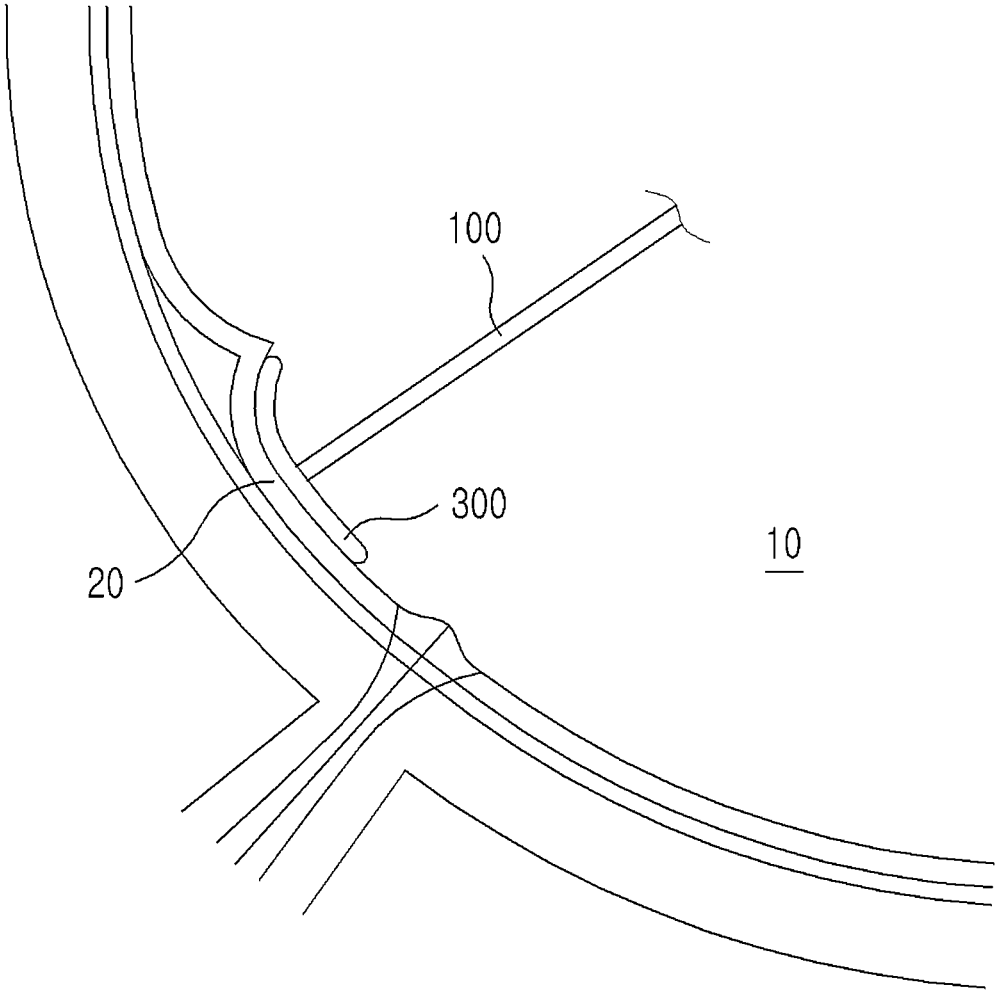
FIG. 6 is an exemplary view for explaining a process of discharging retinal fluid from an eye using a safety vitreous body cutting device according to an embodiment of the disclosure.

FIG. 6 is an exemplary view for explaining a process of discharging retinal fluid from an eye using a safety vitreous body cutting device according to an embodiment of the disclosure.

As shown in FIG. 6, the unfolded safety net part 300 may function to drain subretinal fluid during retina detachment surgery. That is, in retina detachment surgery, a process of extracting the liquid under the detached retina (subretinal fluid drainage) is necessary.

Conventionally, subretinal fluid is drained using the suction power of a vitreous body cutter, or subretinal fluid is drained while being pushed out with a perfluorocarbon (PFO) solution. However, if suction of a vitreous body cutter is used as in the past, there is a risk that the retina is sucked in together and cut. In addition, if perfluorocarbon liquid is used, there is a risk of complications such as necrosis of the retinal cells if the perfluorocarbon liquid flows into the retina slit.

However, as in the disclosure, if the retina 20 is pressed with the unfolded safety net part 300 to discharge the retina fluid, there is no need to use suction power, and since liquid such as perfluorocarbon liquid does not enter the retina slit, it is possible to improve safety. That is, as in the disclosure, if the retina 20 is pressed with the unfolded safety net part 300 to discharge the retina fluid, the retina fluid may be discharged more safely and effectively.

In particular, since the unfolded safety net part 300 is formed to have a certain curvature and is formed of silicone so that elastic shape deformation is possible, the retina 20 may be pressed evenly and with a uniform power, and accordingly, discharge of the retina fluid may be more effective. Preferably, the curvature of the unfolded safety net part 300 may be formed to correspond to the inner curvature of the eyeball.

Figure 7:
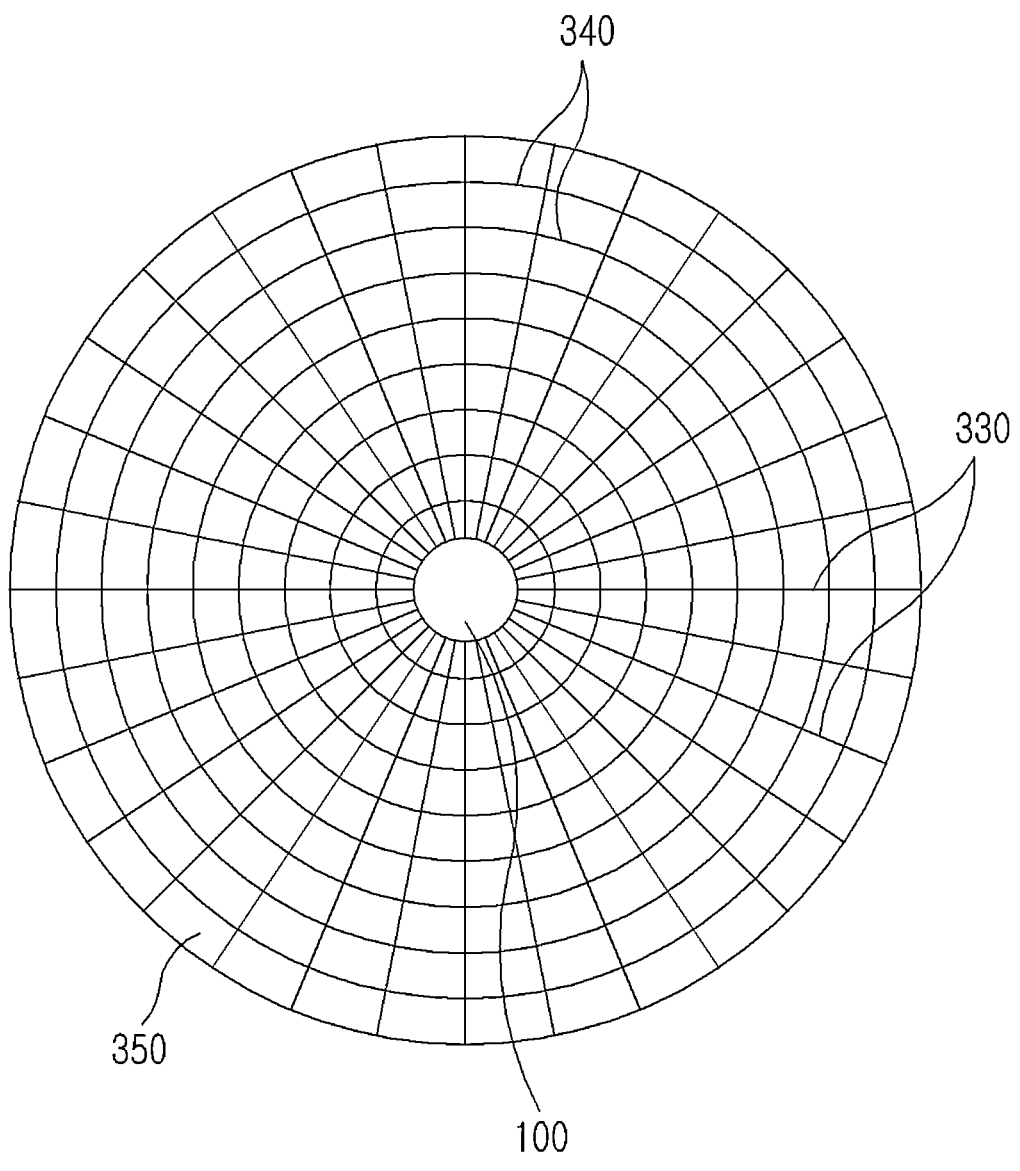
FIG. 7 is a frontal view showing a safety net part of a safety vitreous body cutting device according to another embodiment of the disclosure.
Figure 8:
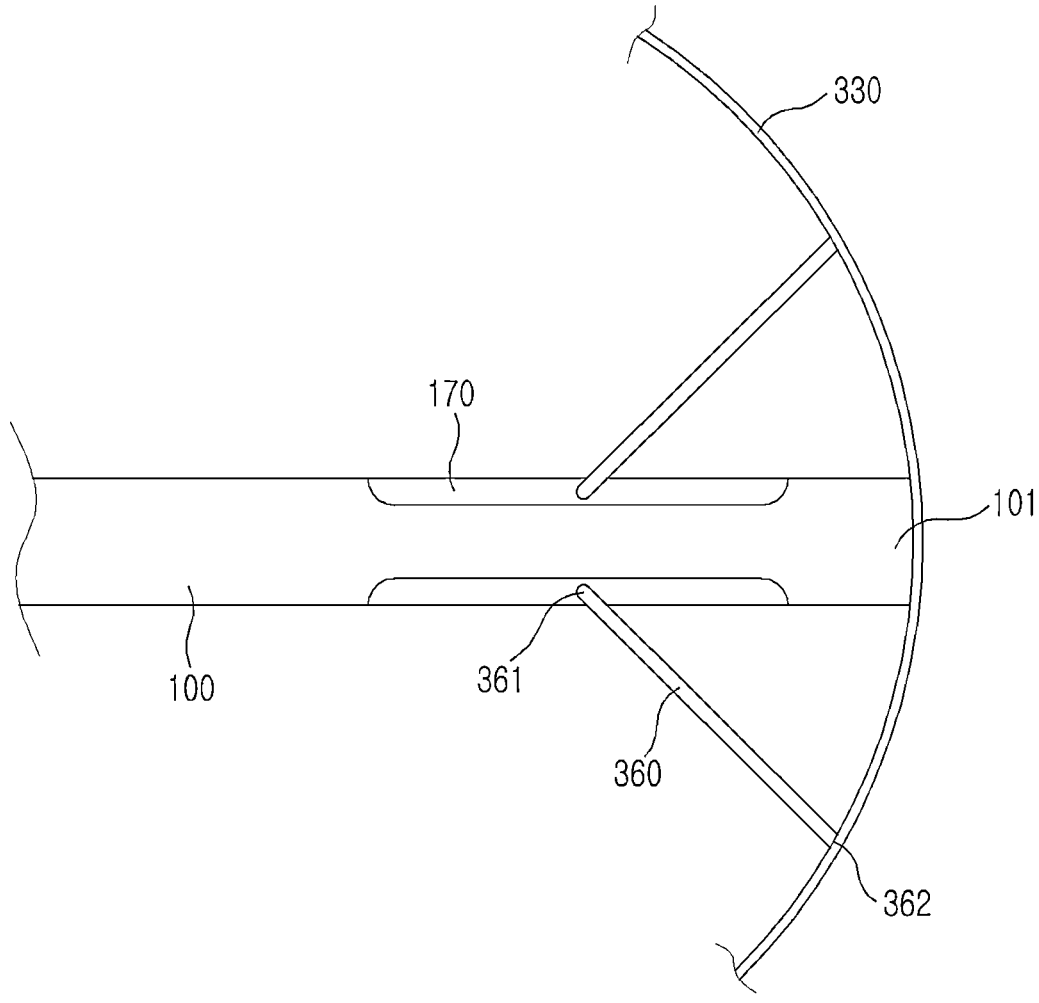
FIG. 8 is a side view showing a safety net part of a safety vitreous body cutting device according to another embodiment of the disclosure.

FIG. 7 is a frontal view showing a safety net part of a safety vitreous body cutting device according to another embodiment of the disclosure, and FIG. 8 is a side view showing a safety net part of a safety vitreous body cutting device according to another embodiment of the disclosure. In this embodiment, the basic configuration of the tubular body part and the cutter part may be the same as in the above-described embodiment, and the safety net part may be different from the above-described embodiment.

As shown in FIG. 7 and FIG. 8, the safety net part 300 according to the present embodiment may have a first frame 330 and a second frame 340.

The first frame 330 may be radially provided at the distal end 101 of the tubular body part 100.

The first frame 330 may be radially provided in the number of 16 to 32 to form a skeleton. The first frame 330 may be formed with a thickness of 0.02 mm.

The second frame 340 may be provided circumferentially on the first frame 330 with different diameters. The second frame 340 may form a mesh 350 together with the first frame 330. Each second frame 340 may be formed concentrically.

The second frame 340 may be formed with a thinner thickness than the first frame 330. For example, the second frame 340 may be formed with a thickness of 0.01 mm and may be provided in the number of 20 to 30.

The first frame 330 and the second frame 340 may be formed of silicone material. Therefore, the first frame 330 may be folded or unfolded around the distal end 101 of the tubular body part 100, and the safety net part 300 may be deformed in shape to be folded or unfolded.

In addition, the safety net part 300 may further have a third frame 360.

One end 361 of the third frame 360 may be connected to the first frame 330. In addition, the other end 362 of the third frame 360 may be provided to slide along the axial direction of the tubular body part 100 on the circumferential surface of the tubular body part 100.

When the other end 362 of the third frame 360 moves toward the distal end 101 of the tubular body part 100, the first frame 330 and the second frame 340 may be unfolded. In addition, when the other end 362 of the third frame 360 moves toward the proximal end 102 of the tubular body part 100, the first frame 330 and the second frame 340 may be folded.

The tubular body part 100 may have a sliding groove 170, and the sliding groove 170 may be formed in the axial direction of the tubular body part 100 on the circumferential surface of the tubular body part 100. The other end 362 of the third frame 360 may be inserted into the sliding groove 170 and slid, and the movement may be guided by the sliding groove 170.

The thickness of the third frame 360 may be 0.02 mm.

When the safety net part 300 is folded, the first frame 330 and the third frame 360 are positioned along the circumference of the tubular body part 100, so the thickness of the first frame 330 and the third frame 360 centered on the tubular body part 100 may be 0.8 mm. Normally, in vitreous body excision surgery, a corneal perforation is made with a thickness of 25 to 27 gauges, so when using the safety vitreous body cutting device according to the disclosure, a corneal perforation of 23 to 25 gauges is to be made. Therefore, this may be compatible with the existing corneal perforation size.

Meanwhile, the safety net part 300 may be formed of a shape memory polymer. In addition, the safety net part 300 may be folded around the distal end 101 of the tubular body part 100, and its shape may be deformed to unfold when inserted into the eyeball.

In the case where the safety net part 300 is formed of a shape memory polymer, the safety net part 300 may have the shape described in FIGS. 4 and 5. Alternatively, the safety net part 300 may have all the shapes described in FIG. 7, and the configuration of the third frame may be omitted.

A method for manufacturing the safety net part 300 using a shape memory polymer is as follows.

First, the safety net part may be manufactured at 36.5° C., which is the temperature of the human body. At this time, the safety net part may be manufactured in an unfolded form.

Afterwards, the safety net part manufactured in an unfolded state may be compressed into a folded form at 60° C. Specifically, the safety net part manufactured in an unfolded state may be heat-treated in a folded state at 60° C. for 3 minutes.

The safety net part manufactured in this way may have a deformation recovery rate of 90% or more at body temperature, which is restored to its initial state, that is, the unfolded state.

The description of the disclosure is for illustrative purposes, and those skilled in the art will understand that it can be easily modified into other specific forms without changing the technical idea or essential features of the disclosure. Therefore, the embodiments described above should be understood as being exemplary in all respects and not limiting. For example, each component described as a single type may be implemented in a distributed manner, and likewise, components described as distributed may be implemented in a combined form.

The scope of the disclosure is indicated by the following claims, and all changes or modifications derived from the meaning and scope of the claims and their equivalent concepts should be interpreted as being included in the scope of the disclosure.

The description of the disclosure is for illustrative purposes, and those skilled in the art will understand that it can be easily modified into other specific forms without changing the technical idea or essential features of the disclosure. Therefore, the embodiments described above should be understood as being exemplary in all respects and not limiting. For example, each component described as a single type may be implemented in a distributed manner, and likewise, components described as distributed may be implemented in a combined form.

The scope of the disclosure is indicated by the following claims, and all changes or modifications derived from the meaning and scope of the claims and their equivalent concepts should be interpreted as being included in the scope of the disclosure.

EXPLANATION OF REFERENCE NUMERALS

100: tubular body part
110: open hole
170: sliding groove
200: cutter part
300: safety net part
310: sheet
320: through-hole
330: first frame
340: second frame
350: mesh
360: third frame

What is claimed is:

1. A safety vitreous body cutting device, comprising:
a tubular body part having a cylindrical shape, in which a negative pressure is provided at an inside and an open hole is defined on a circumferential surface of a distal end;
a cutter part configured to reciprocate along an axial direction of the tubular body part at the inside of the tubular body part and configured to cut a vitreous body introduced into the open hole; and
a safety net part that is positioned at the distal end of the tubular body part to allow the vitreous body to pass through but prevent a retina tissue from passing through,
wherein the safety net part has a disc-shaped sheet of which a central part is connected to a distal most end of the tubular body part, and a plurality of through-holes formed through the disc-shaped sheet.

2. The safety vitreous body cutting device of claim 1, wherein each of the plurality of through-holes is formed in a square shape with vertical and horizontal lengths of 0.09 to 0.11 mm.

3. The safety vitreous body cutting device of claim 1, wherein the safety net part includes silicone material and is configured to fold or unfold around the distal end of the tubular body part.

4. The safety vitreous body cutting device of claim 1, wherein the safety net part has
a first frame radially disposed at the distal end of the tubular body part, and
a second frame circumferentially connected to the first frame with different diameters to form a mesh together with the first frame.

5. The safety vitreous body cutting device of claim 4, wherein the safety net part further has
a third frame having one end connected to the first frame and another end provided to slide along the axial direction of the tubular body part on the circumferential surface of the tubular body part, thereby allowing the first frame to fold or unfold around the distal end of the tubular body part.

6. The safety vitreous body cutting device of claim 5, wherein
a sliding groove is formed on the circumferential surface of the tubular body part to guide the another end of the third frame to be inserted and slide.

7. The safety vitreous body cutting device of claim 4, wherein
the safety net part includes silicone material and is configured to fold or unfold around the distal end of the tubular body part.

8. The safety vitreous body cutting device of claim 4, wherein
the safety net part includes a shape memory polymer, and
the safety net part, which is in a state of being folded around the distal end of the tubular body part, deforms in shape to unfold when inserted into an eye.

9. The safety vitreous body cutting device of claim 1, wherein
the safety net part has a circular shape with a diameter of 6 to 7 mm.

* * * * *